United States Patent [19]

Chu

[11] Patent Number: 5,175,267
[45] Date of Patent: Dec. 29, 1992

[54] STEREOSELECTIVE GLYCOSYLATION OF HETERCYCLIC BASES

[75] Inventor: Chung K. Chu, Athens, Ga.

[73] Assignee: University of Georgia Research Foundation, Inc., Athens, Ga.

[21] Appl. No.: 487,542

[22] Filed: Mar. 2, 1990

[51] Int. Cl.$^5$ .................. C07H 17/00; C07H 19/06
[52] U.S. Cl. ................................ 536/26; 536/23; 536/24
[58] Field of Search ................. 536/24, 23, 26

[56] References Cited

U.S. PATENT DOCUMENTS 4,230,689 10/1980 Choy .............................. 424/195.1
4,230,698 10/1980 Bobek et al. ..................... 536/24

OTHER PUBLICATIONS

Fleet, Son and Drome, *Tetrahedron* 42(2), 625 (1988).
Chu, C. K., Beach, J. W., Ullas, G. V. & Kosugi, Y. in *Tetrahedron Lett.* 29,5349 (1988).
Chu, et al. *Nucleosides and Nucleotides* 8(5&6), 903 (1989).
Okabe, M., et al, *J. Org. Chem.* 53,4780 (1988).
Farina, V., and Benigni, D. A., *Tetrahedron Lett.* 29,1239 (1988).
Niedballa, U. and Vorbruggen, H., *J. Org. Chem.* 39 (25) 1974.
Hanessian and Murray, *Tetrahedron* 43, 5055, (1987).
Jones, D. N., Mundy, D., and Whitehouse, R. D., *J. Chem. Soc. Chem. Comm.* 86 (1970).
Nozaki, K., and Oshima, K., *Tetrahedron Lett.* 29, 6125 (1988).

*Primary Examiner*—Johann Richter
*Attorney, Agent, or Firm*—Kilpatrick & Cody

[57] ABSTRACT

A method of preparation of 2',3'-dideoxy and 2',3'-dideoxy-2',3'-didehydronucleosides that includes the step of condensing a 1-O-activated-2-(aromatic or aliphatic)-selenenyl-5-O-protected ribose with a protected heterocyclic base in the presence of trimethylsilyl triflate or a Lewis acid to form a β-anomeric nucleoside in high yield.

10 Claims, 1 Drawing Sheet

R = SiPh₂t-Bu
Ph = phenyl
Me = CH₃
Bu = Butyl
Et = ethyl (a) Li-HMDS, -78°C, (CH₃)₃SiCl, -78°C → r.t., THF;
(b) -78°C, PhSeBr;   (c) DBU or diethylamine, THF;
(d) DIBAL, toluene, -78°C   (e) Ac₂O/Py, 0°C;
(f) Silylated thymine, TMSOTf, ClCH₂CH₂Cl;
(g) 10% H₂O₂, cat. Py.;   (h) n-Bu₄NF, THF;
(i) n-Bu₃SnH, Et₃B, benzene, RT.

STEREOSELECTIVE GLYCOSYLATION OF HETERCYCLIC BASES

The government has rights in this invention by virtue of grants from the Public Health Service and the National Institute of Allergy and Infectious Diseases.

This invention is in the area of synthetic organic chemistry, and is in particular a highly stereoselective method of glycosylation of heterocyclic bases to obtain β-anomeric nucleosides.

A nucleoside is a molecule consisting of a 4-carbon sugar and a purine or pyrimidine base. Addition of a phosphate group to the 5' position of the nucleoside converts the nucleoside into a nucleotide. Natural nucleotides are the building blocks for the nucleic acids, RNA (ribonucleic acid) and DNA (deoxyribonucleic acid).

In 1985, it was reported that the synthetic nucleoside 3'-azido-3'-deoxythymidine (AZT) inhibits the replication of human immunodeficiency virus type 1 and type 2 (HIV-1 and HIV-2, generally referred to below as HIV). Mitsuya, H., et al., *Proc. Natl. Acad. Sci. U.S.A.* 82, 7096 (1985). These two viruses are believed to cause acquired immunodeficiency syndrome (AIDS).

AIDS is characterized by an imbalance in two basic types of immune system cells, helper/inducer T lymphocytes and suppressor T lymphocytes, with the ratio of suppressor cells to helper/inducer cells greatly elevated. Helper/inducer T cells, defined by a surface antigen called CD4, are responsible for the induction of most of the functions of the human immune system, including the humoral immune response involving the production of antibodies by B lymphocytes and the cell-mediated response involving stimulation of cytotoxic T cells. A condition associated with HIV is AIDS-related complex, or ARC. Most patients suffering from ARC eventually develop AIDS.

Since the initial discovery of the antiviral activity of 3'-azido-3'-deoxythymidine (AZT) against human immunodeficiency virus (HIV), a number of other deoxynucleosides have been found to possess potent anti-HIV activity in vitro, including 3'-azido-2',3'-dideoxyuridine (alternatively named AzddU, AZDU or CS-87) (Eriksson, B. F. H., Chu, C. K., and Schinazi, R. F., *Antimicrob. Chemother.* 33, 1729 (1989); Chu, C. K., et al., *J. Med. Chem.* 32, 612 (1989)), 2',3'-dideoxycytidine (D2C) (Mitsuya, H. and Broder, S. *Proc. Natl. Acad. Sci. U.S.A.* 83, 1911 (1986)), 2',3'-dideoxyinosine (D2I) (Yarchoan, R., et. al., S. *Science* 245, 412 (1989)), 3'-deoxy-2',3'-didehydrothymidine (D4T) (Mansuri, M. M., et al., *J. Med. Chem.* 32, 461 (1989)), and 2',3'-dideoxy-N6-methyladenosine (D2MeA) (Chu and Schinazi, *Biochem. Pharmacol.* 37(19) 3543 (1988)). Many of these nucleosides are currently being evaluated for toxicity and efficacy in patients diagnosed with AIDS and AIDS-related complex.

Nucleosides with potent anticancer activity are also well known. The active antiviral and antibiotic nucleosides all exist in a β-anomeric configuration (i.e., the base is bonded to the 1-position of the sugar through a β bond).

In light of the profound importance of these compounds in the treatment of seriously ill patients, there is a strong need for methods for their manufacture that are efficient and cost effective.

2',3'-Dideoxynucleosides have historically been prepared by either of two routes; condensation of a sugar moiety with a nitrogenous base, and derivatization of a preformed nucleoside.

Synthetic schemes for the preparation of nucleoside derivatives from preformed nucleosides include those described by: Dyatkina, N. B., *Soviet J. Biorg. Chem.* 12, 563 (1986); Colla, et al., *Eur. J. Med. Chem.—Chim. Ther.* 20(4), 295 (1985); Herdewijn, et al., *J. Med. Chem.* 30, 1270 (1987); Horowitz, et al., *J. Org. Chem.* 29, 2076 (1984); Krenitsky, et al., *J. Med. Chem.* 26(6), 891 (1983); and Webb, et al., *Nucleosides and Nucleotides* 7(2), 147 (1988).

The original synthesis of AZDU was reported by Lin and Mancini, starting from 2'-deoxyuridine. Lin, T. S., and Mancini, W. R., *J. Med. Chem.* 26, 544 (1983). The first step in the Lin scheme is the mesylation of the 3'-position of a 5'-protected-2'-deoxynucleoside. Treatment with base provides the 2,3'-anhydro nucleoside derivative, that is acidified and again mesylated to form the 1-[2-deoxy-3-O-methanesulfonyl-5-O-(protected)-β-D-threo-pentofuranosyl]nucleoside. This compound is then reacted with azide ion and then deprotected to produce a 3'-azido-2',3'-dideoxynucleoside. D4T has also been synthesized from thymidine (Horwitz, J. P., et al., *J. Org. Chem.* 31, 205 (1966)), and a slightly modified procedure is now being used for a large scale preparation. (Martin, J. C., et al., *Nucleosides and Nucleotides* 8, 841 (1989)).

While the Lin and Mancini reaction scheme is suitable for the industrial preparation of 3'-substituted-2',3'-dideoxynucleosides, it is limited because the starting material, 2'-deoxynucleoside, is difficult to obtain and prohibitively expensive. The other reported methods of preparation of nucleosides by derivatization of preformed nucleosides are generally suitable only as laboratory syntheses to obtain small amounts of compound for experimental use, but are not well suited for industrial scale preparation of the compounds, because of the number of steps required to obtain the product and the cost of nucleoside starting material.

Synthetic schemes for the preparation of nucleoside derivatives that include the step of condensing a sugar with a nitrogenous base are described in U.S. Pat. No. 4,230,689 to Bobek, et al. and by Fleet, Son and Drome, *Tetrahedron* 42(2), 625 (1988).

A novel synthesis of AZDU from an α,β-unsaturated gamma-butyrolactone was described by Chu, C. K., Beach, J. W., Ullas, G. V., and Kosugi, Y., in *Tetrahedron Lett.* 29, 5349 (1988). In this synthetic scheme, the azide moiety is introduced into the lactone through a Michael reaction to obtain a derivatized carbohydrate, which is then condensed with a silylated uridine to form the derivatized nucleoside. In this reaction scheme, however, glycosylation yields a mixture of 2 to 1 β anomer to α anomer, reducing the efficiency of reaction.

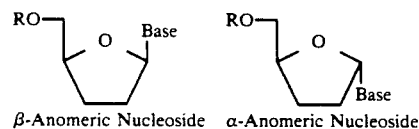

β-Anomeric Nucleoside    α-Anomeric Nucleoside

Chu, et. al., attempted to increase the ratio of β to α anomer by placing a thiophenol group in the 3-position of the gamma-butyrolactone before condensation with base, with the strategy that the bulky α-substituent would direct the base to the β-position. Chu, et. al.,

*Nucleosides and Nucleotides* 8(5 and 6), 903 (1989). However, the ratio of α to β anomer was 1:1, and the anomers were not easily separated.

The synthesis of D2C by the condensation of a 2,3-dideoxyribose derivative and cytosine gave similarly poor stereoselectivity (Okabe, M., et al., *J. Org. Chem.* 53, 4780 (1988); Farina, V., and Benigni, D. A., *Tetrahedron Lett.* 29, 1239 (1988)).

Niedballa and Vorbruggen have investigated the effect of substituent groups on the condensation of various ribofuranose, ribopyranose, and glucopyranose derivatives with silylated bases in the presence of Friedel-Crafts catalysts. Niedballa, U. and Vorbruggen, H., *J. Org. Chem.* 39 (25) 1974. The catalyst abstracts the alkoxy or acyloxy group from the 1-position of the sugar, producing a carbocation in the 1-position that is susceptible to attack by the silylated base from either above the plane of the ring (forming a β-isomer) or below the plane of the ring (forming an α-isomer). They discovered that the presence of a 2-acyloxy group in the sugar moiety increased the percentage of β-anomeric nucleoside product, and it was hypothesized that the 2-acyloxy group stabilizes the positive charge at the 1-position by forming a 1,2-α-acyloxonium salt intermediate. Niedballa and Vorbruggen found that condensation of a 2-deoxy-D-ribose with a silylated base resulted in a consistent ratio of β/α anomers of 1/1 that could not be changed by manipulation of reaction conditions.

The Niedballa approach to stereoselective glycosylation requires the presence of a 2-acyloxy or 2-benzoyl group in the sugar moiety. The majority of the pharmaceutically active nucleosides are deoxygenated in the 2'-position. If the Niedballa route is used for the preparation of these compounds, the 2-acyloxy group or 2-benzoyl group must be removed after condensation with the base, through a multistep procedure such as preparation and reduction of a 2',3'-cyclic orthoformate or a dithiocarbonate. This decreases the efficiency and increases the cost of the reaction scheme.

The synthesis of 2',3'-dideoxy-2',3'-didehydronucleosides by the condensation of a 2,3-unsaturated ribose with the desired base is not a commercially viable route to these compounds because the starting material, 2,3-unsaturated ribose, is highly unstable.

The problems described above that are encountered in the preparation of pharmaceutically active nucleosides increase the cost of health care and result in shortages of severely needed antiviral compounds. Further, the high cost of the antiviral, and in particular anti-HIV, nucleosides prevents many of those in need from being able to obtain the drug.

There is a strong need for a method of synthesis of 2',3'-dideoxy and 2',3'-dideoxy-2',3'-didehydronucleosides that has a minimal number of steps and a high yield of product. In addition, it is desirable to have a synthetic scheme for D4T that does not require thymidine as a starting material, given the high demand for thymidine as the starting material for AZT.

It is therefore an object of the present invention to provide a method of synthesis of 2',3'-dideoxy and 2',3'-dideoxy-2',3'-didehydronucleosides that is efficient and convenient It is another object of the present invention to provide a method of synthesis of 2',3'-dideoxy and 2',3'-dideoxy-2',3'-didehydronucleosides that provides a high ratio of β to α anomer.

SUMMARY OF THE INVENTION

The present invention is a method of preparation of 2',3'-dideoxy and 2',3'-dideoxy-2',3'-didehydronucleosides that includes the step of condensing a 1-O-activated-2-(aromatic or aliphatic)-selenenyl-5-O-protected ribose with a protected heterocyclic base in the presence of trimethylsilyl triflate or a Lewis acid to form a β-anomeric nucleoside in high yield. This stereoselective glycosylation is highly suited to the industrial manufacture of biologically active nucleosides because it provides a high yield of product in a minimal number of steps using moderately priced starting materials.

According to this method, (S)-5-O-protected-3,4-dihydro-2(5H)-furanone is first reacted with a strong base and a silyl halide to produce the corresponding 1-silyl enol ether (See FIG. 1). The enol ether is then reacted in situ with an aromatic or aliphatic selenium halide to produce 5-O-protected-3,4-(dihydro)-3-(α and β)-(aromatic or aliphatic)-selenenyl-2(5H)-furanone. The α-aromatic or aliphatic selenenyl furanone, the predominant product of reaction, is then reduced to the corresponding 5-O-(protected)-2,3-dideoxy-2-selenenyl ribose and activated at the 1-position by acetylation, alkylation, or halogenation. In an alternative embodiment, an aromatic or aliphatic disulfide is substituted for the selenium halide.

The β-anomeric nucleoside is produced in high yield by stereoselective glycosylation of a protected base with the 1-O-activated-2,3-dideoxy-2-(aromatic or aliphatic)selenenyl-5-0-O-(protected)-ribose in the presence of trimethylsilyl triflate or a Lewis acid. It has been discovered that the presence of the 2-selenenyl (or sulfonyl) derivative in the ribose during condensation is essential to the stereoselectivity of this reaction scheme. The selenenyl derivative may direct glycosylation in two ways: by steric hindrance of the attack by the base at the 1-position below the plane of the ribose; or alternatively through a "neighboring group effect" by which the aromatic or aliphatic selenenyl group stabilizes the positive charge at the 1-position through a cyclic intermediate and directs base addition in the β-position.

In the final step, the aliphatic or aromatic selenenyl group is either oxidatively removed to produce a 2',3'-dideoxy-2',3'-didehydronucleoside, or reductively removed to produce a 2',3'-dideoxynucleoside.

DETAILED DESCRIPTION OF THE INVENTION

Figure 1:
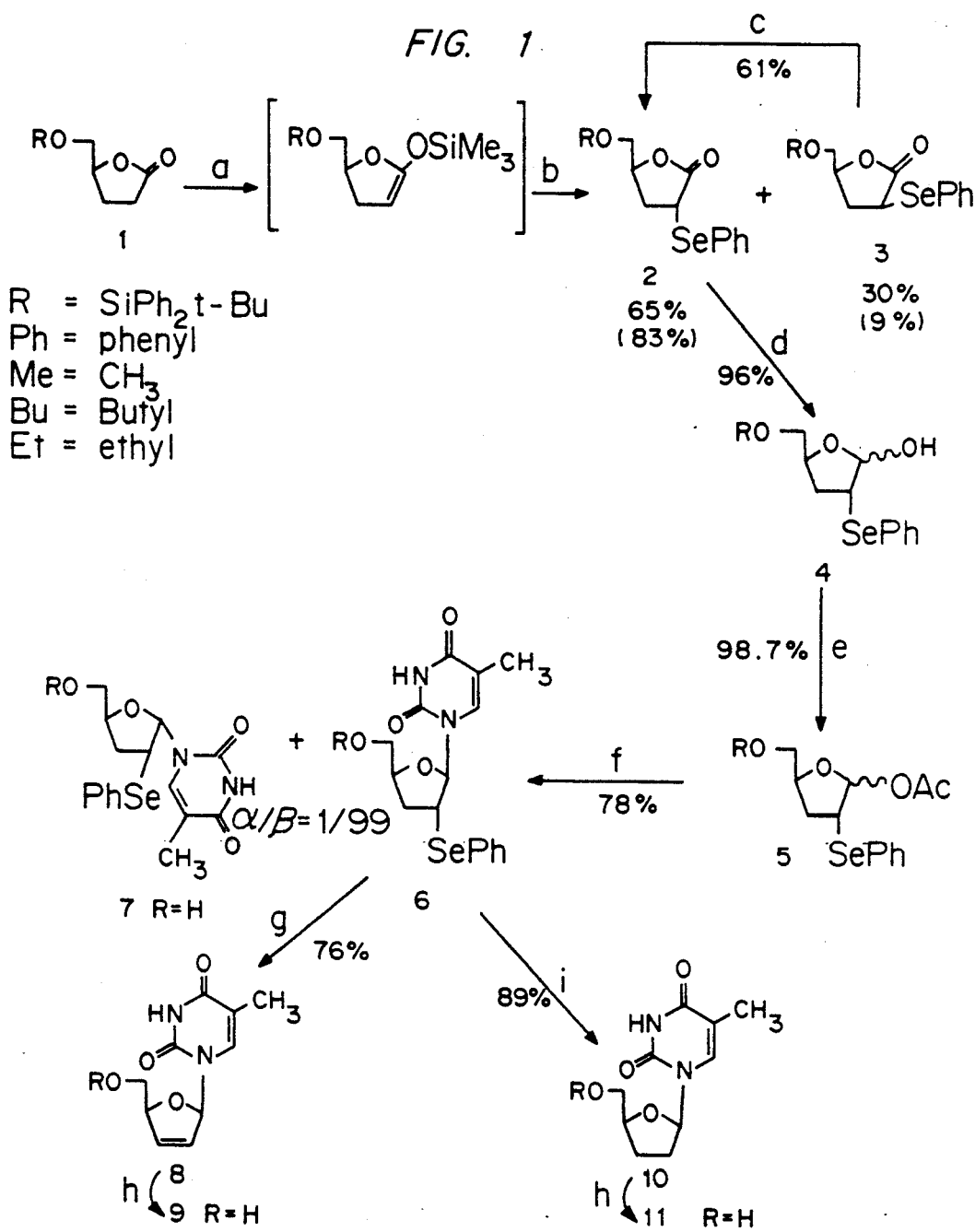
FIG. 1 is a schematic illustration of the stereoselective preparation of 3'-deoxythymidine (D2T) and 3'-deoxy-2',3'-didehydrothymidine (D4T).

I. Preparation of the 1-Silyl Enol Ether of (S)-5-O-Protected-3,4-Dihydro-2(5H)-Furanone The starting material for this method of preparation of 2′,3′-dideoxy and 2′,3′-dideoxy-2′,3′-didehydronucleosides is (S)-5-O-protected-3,4-dihydro-2(5H)-furanone 1 (see FIG. 1), which is easily prepared from a variety of starting materials. Methods for the preparation of this compound are described in Taniguchi, M., et. al., *Tetrahedron* 30, 3547 (1974); Ravid, U., et al., *Tetrahedron* 34, 1449 (1978); Takano, S., et al., *Heterocycles* 16, 951 (1981); Camps, P., et al., *Tetrahedron* 38, 2395 (1982); and Lundt, I., et al., *Synthesis* 1052 (1986).

Suitable protecting groups for the 5-hydroxyl group of the furanone are known to those skilled in the art, and include trisubstituted silyl groups such as trimethylsilyl, dimethylhexylsilyl, t-butyldimethylsilyl, and t-butyldiphenylsilyl; trityl; alkyl groups; acyl groups such as acetyl, propionyl, benzoyl, p-$NO_2$ benzoyl, and toluyl; methylsulfonyl, and p-toluylsulfonyl.

In the first step of this method (see FIG. 1), compound 1 is converted to the corresponding 1-silyl enol ether by abstracting a hydrogen from the 2-position of the furanone with a strong base and then reacting the enol with a silyl halide in situ. Any base is suitable that is capable of abstracting the 2-hydrogen. A preferred base is lithium bis(trimethylsilyl)amide (Li-HMDS). Other appropriate bases include lithium ethoxide, potassium t-butoxide and lithium diisopropylamide (LDA).

Lithium enol ethers are not preferred in the overall reaction scheme because the lithium enolate of the furanose is not selenylated or sulfenylated easily.

Suitable silyl halides include chlorotrimethylsilane, chlorodimethylhexylsilane, chloro-t-butyldimethylsilane, and chloro-t-butyldiphenylsilane.

Methods and reagents to prepare silyl enol ethers are described in House, et al., *J. Org. Chem.* 34, 2324 (1969); Rasmusssen, et al., *Tet. Letters* 2738 (1973); and Rasmussen, J., and Hassner, A., *J. Org. Chem.* 39, 2558 (1974).

In the typical reaction, the furanone derivative is dissolved in a dry organic solvent that does not have active hydrogens, for example tetrahydrofuran (THF), and the temperature is cooled to between $-10°$ and $-100°$ C. A dry ice-acetone bath can be used to cool the solution to approximately $-78$ C. The solution should be maintained in a moisture free environment by flushing the reaction vessel with an inert gas such as argon or nitrogen. The base is then added and the solution stirred at the reduced temperature until the enolate is formed, which typically takes one hour or less. The silyl halide is then added dropwise, and after addition is complete, the reaction solution is allowed to warm to room temperature.

II. Preparation of 5-O-Protected-3,4-Dihydro-3-(α)-Aromatic or Aliphatic Selenenyl-2(H)-Furanone In the second step of the reaction scheme, the 1-silyl enol ether of (S)-5-O-protected-3,4-dihydro-2(5H)-furanone is reacted with an aromatic or aliphatic selenium halide to produce a 5-O-protected-3,4-dihydro-3-(α or β)-aromatic or aliphatic selenenyl-2(H)-furanone in high yield. If the selenium derivative approaches from below the plane of the furanone, an α-selenenyl anomer is produced; if it approaches from above the plane of the furanone, a β-selenenyl anomer is produced. It is the α-selenenyl anomer that is required in the subsequent stereoselective glycosylation step.

Any aromatic or aliphatic selenenyl halide can be used that will react with the furanone and direct glycosylation in the condensation reaction. The suitability of the compound can be easily evaluated by carrying out the procedure described in Example 1. Examples of suitable selenenyl halides include phenylselenenyl bromide and phenylselenenyl chloride, wherein the phenyl group is optionally substituted with nitro, cyano, or alkyl groups; and $C_1$ to $C_{25}$ alkyl selenenyl bromides or chlorides, wherein the alkyl moiety is optionally substituted with nitro, cyano, or aromatic groups. For a general treatise on methods of synthesis of organic selenenyl halides see: Paulmeier, Claude *Seneneyl Reagents and Intermediates in Organic Chemistry* Pergamon Press 1986 (New York). The selenenyl bromides can be prepared in situ from equimolar quantities of bromine and diphenyl or dialkyl selenide. Reich, et al., *J. Am. Chem. Soc.* 97, 5354 (1975).

The phenylselenenyl group is preferred because of the ease with which it can be removed as well as its chemical stability during synthesis. It has been reported that selenylation and deselenylation is an effective route to the preparation of 5-O-t-butyldiphenylsilyl-2,3-dideoxy-2,3-didehydroribonolactone from (5)-H-furan-2-one. Hanessian and Murray, *Tetrahedron* 43, 5055 (1987). However, it has never been predicted that a selenenyl group in the 2-position of a furanone would dramatically influence glycosylation of a heterocyclic base.

The silyl enol ether should be reacted with the selenium halide at a low temperature, preferably between $-10°$ and $-100°$ C., and most preferably at $-78°$ C. Ryu, I., et al., *Synthesis* 874 (1977). It is preferred to first generate the silyl enol ether in situ, cool the solution to the desire temperature, and then add the selenium halide. The reaction can be monitored by thin layer chromatography according to methods known to those skilled in the art.

In order to obtain the desired C2-α-isomer 3 as the major product, a bulky group such as t-butyldiphenylsilyl, dimethylhexylsilyl, or t-butyldimethylsilyl should be used as the protecting group for the 5-OH. The t-butyldiphenylsilyl group is preferred. For example, the reaction of the 1-silyl enol ether of (S)-5-O-t-butyldiphenylsilyl-3,4-dihydro-2(5H)-furanose with phenylselenium bromide provides a yield of 65% of C2-α isomer 3 along with 30% of the C2-β isomer 4.

It has been discovered that the isolated β-isomer 4 can be converted to predominately the α-isomer by treatment with a base such as 1,8-diazabicyclo[5.4.0]under-7-ene (DBU) or diethylamine. This increases the efficiency of the overall reaction scheme, and decreases the cost of the final product.

In an alternative embodiment, an aliphatic or aromatic sulfenyl moiety is added to the 2-position of the furanone in place of the selenenyl compound. The sulfenyl group can be added to the furanone by reacting the corresponding disulfide with the furanone under the conditions described above for the addition of the selenenyl compound.

III. Activation of the 1-O Position

In the third step of this method, the 5-O-protected-3,4-dihydro-3-(α)-aromatic or aliphatic selenenyl-2(H)-furanone is reduced to the corresponding 5-O-(t-butyl-diphenylsilyl)-2,3-dideoxy-2-aromatic or aliphatic selenenyl ribose, and then activated at the 1-O position by acylation, alkylation, or halogenation (Cl or Br).

Suitable reducing agents include diisobutylaluminum hydride (DIBAL-H), lithium borohydride (LiBH$_4$), sodium bis(2-methoxyethoxy)aluminum hydride (Red-Al), or other sterically hindered reducing agents known to those skilled in the art. Reduction can be accomplished under known conditions, including dropwise addition of the reducing agent to a dry organic solution of the furanone under argon or nitrogen. The reaction is monitored for completeness with thin layer chromatography (TLC). When the TLC indicates the disappearance of starting material, the reaction is quenched by the addition of alcohol.

The 1-O-acetate can be prepared by mixing the ribose with acetic acid or acetic anhydride in dry pyridine at low temperature, preferably 0°–5° C. The corresponding halide can be prepared by reacting the acetate with hydrogen chloride or bromide. Alternatively, the ribose can be reacted with an alkyl halide to form an ether, according to known methods. Again, these reactions can be monitored for completeness with TLC.

It has been found that compound 5 is fairly unstable, and therefore, preferably used as is in the condensation reaction without further purification.

IV. Condensation of the Base with the Ribofuranose Derivative

In the fourth step of this reaction scheme, the highly stereoselective glycosylation of the desired protected heterocyclic base with 1-O-activated-2,3-dideoxy-2-aromatic or aliphatic selenenyl-5-O-protected ribose is accomplished in the presence of trimethylsilyl triflate (trimethylsilyl trifluoromethanesulfonate) or a Lewis acid in a dry organic solvent.

Any compound containing a nitrogen that is capable of reaction with a center of electron deficiency can be used in the condensation reaction. Purine bases include adenine, hypoxanthine, N$^6$-alkylpurines, N$^6$-benzylpurine, N$^6$-halopurine, and guanine. Pyrimidine bases include thymine, cytosine, 6-azapyrimidine, 2-mercaptopyrimidine, and uracil.

Functional oxygen and nitrogen groups on the heterocyclic base should be protected before condensation with the sugar. Protecting groups are well known to those skilled in the art, and include trimethylsilyl, dimethylhexylsilyl, t-butyldimethylsilyl, and t-butyldiphenylsilyl; tritylmethyl; alkyl groups; acyl groups such as acetyl and propionyl; methylsulfonyl, and p-toluylsulfonyl.

Friedel-Crafts catalysts (Lewis acids) that can be used in the condensation reaction include SnCl$_4$, ZnCl$_4$, TiCl$_4$, AlCl$_3$, FeCl$_3$, BF$_3$-diethylether, and BCl$_3$. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Anhydrous aluminum chloride is not soluble in carbon disulfide. Niedballa, et al., *J. Org. Chem.* 39, 25 (1974). The preferred catalyst is SnCl$_4$. The preferred solvent is 1,2-dichloroethane.

The amount of catalyst needed to facilitate reaction depends on the reactivity of the 1-O-substituent. For example, the condensation of a 1-O-halo furanose usually requires 0.25 equivalents of catalyst, whereas a 1-O-alkyl or 1-O-acyl furanose may require from 0.75 to 1.5 equivalents of catalyst.

Trimethylsilyl triflate can be used under the same conditions described above for the Friedel-Crafts catalysts. The reaction proceeds at a temperature range of from −10° C. to 200° C.

It has been discovered that a 2-selenenyl or sulfenyl group directs glycosylation almost exclusively to the β-anomeric nucleoside, the pharmaceutically active anomer. This was unexpected because a 3-sulfenyl substituent has no effect on direction of glycosylation. The selenenyl derivative may direct glycosylation in two ways: by steric hindrance of the attack by the base at the 1-position below the plane of the ribose; or alternatively through a "neighboring group effect" by which the aromatic or aliphatic selenenyl group stabilizes the positive charge at the 1-position through a charged cyclic intermediate and directs base addition in the β-position. A neighboring group effect occurs when an electron-deficient carbon is generated (the 1-O-carbocation), and a nearby group (the phenylselenenyl group) helps to relieve the deficiency by donating electron density.

For example, the condensation of 5 (see FIG. 1) and silylated thymine in the presence of trimethylsilyl triflate gave 6 and 7 in the ratio of 99 to 1 in 78% yield. Although TLC and high pressure liquid chromatography (normal phase, 10μ,1% methanol in chloroform) showed the product to be a single isomer, the desilylated product showed approximately 1% α-anomer. Silylated 7 could not be separated from 6 by chromatography due to its low concentration (1%) and the fact that the two compounds have the virtually the same Rf value (TLC) and retention time (HPLC). However, the desilylated compounds could be separated.

V. Oxidative or Reductive Elimination of Selenenyl Moiety

The selenenyl group is then removed either oxidatively to provide a 2',3'-dideoxy-2',3'-didehydronucleoside, or reductively to provide the corresponding 2',3'-dideoxynucleoside.

The oxidative removal of the selenenyl group is achieved by reacting the condensed product with 10% hydrogen peroxide in dichloromethane. Although there are two α-hydrogens (1' and 3') available for syn-elimination of selenoxide, (Jones, D. N., Mundy, D., and Whitehouse, R. D., *J. Chem Soc. Chem. Commun.* 86 (1970)) the elimination proceeds smoothly in the desired direction to give the 5'-O-protected-2',3'-deoxy-2',3'-didehydronucleoside in high yield.

Similarly, the selenenyl group is removed reductively with tri-n-butyltin hydride in the presence of triethylborane (Nozaki, K, and Oshima, K., *Tetrahedron Lett.* 29, 6125 (1988)) in benzene at room temperature to give the desired 5'-O-t-protected-2',3'-dideoxynucleoside.

Sulfenyl groups can be reduced with Raney nickel or oxidized with a peroxide such as m-Cl-perbenzoic acid followed by treatment with potassium t-butoxide, according to methods known to those skilled in the art.

In the final step of this method of preparation of 2',3'-dideoxy and 2',3'-dideoxy-2',3'-didehydronucleosides, the 5-O-position is deprotected. Desilylation can be carried out with a variety of reagents, including acetic acid, trifluoroacetic acid, hydrogen fluoride, n-tetrabutylammonium fluoride, potassium fluoride and pyridinium HCl. Acetic acid is preferred for commercial scale use because it is inexpensive. Other reagents for desilylation are known to those skilled in the art. Deacylation is accomplished in acid or base. 5-O-Ethers can be cleaved with $BCl_3$ or trimethylsilyl iodide.

The stereoselective glycosylation of heterocyclic bases according to the present invention will be better understood with reference to the following nonlimiting examples.

EXAMPLE 1

Preparation of 2',3'-Dideoxy-2',3'-Didehydrothymidine (S)-5[(t-Butyldiphenylsilyloxy)methyl]-3,4-dihydro-3-α and β-phenylselenenyl-2(5H)-furanone (2) and (3)

(S)-5[(t-Butyldiphenylsilyloxy)methyl]-3,4-dihydro-2(5H)-furanone 1 (compound structures are illustrated by number in FIG. 1) (0.708 g, 2 mmol) was dissolved in freshly distilled dry tetrahydrofuran (THF, 5 mL) under argon and cooled to −78° C. in a dry ice-acetone bath. The enolate was prepared by dropwise addition of a 1M solution of lithium bis(trimethylsilyl)amide in THF (2.2 mL, 2.2 mmol). The mixture was allowed to stir for 1 hour at −78° C. Chlorotrimethylsilane (2.5 mmol, 0.32 mL) was then added dropwise to the enolate. After the addition was complete, the reaction mixture was allowed to warm slowly to room temperature. The solution was stirred at room temperature for 0.5 hours, and then cooled to −78° C. again. A solution of phenylselenium bromide (0.708 g, 3 mmol) in THF (3 mL) was added to the reaction mixture dropwise over a period of 15 minutes. After the addition was complete, thin layer chromatography indicated complete disappearance of the starting material. The reaction mixture was poured into ether and washed with water until the organic layer became yellow. The organic layer was then dried over anhydrous sodium sulphate and concentrated to get the crude mixture which was chromatographed over a column of silica gel (230-400 mesh) using ethyl acetate (0-6%) in hexane as the eluent. After the removal of diphenyldiselenide, the α-isomer 2 was obtained in 65% yield (0.662 g). $^1$H-NMR (CDCl$_3$: 250 MHz) δ 1.02 (s, 9 H, 6-Bu), 2.23-2.34 (m, 1 H, 4-H ), 2.64-2.75 (m, 1 H, 4-H$_b$), 3.60 (dd, 1 H, $J_{5,6}$=11.6 $J_{6Ha6Hb}$=3.2 Hz, 6-H$_a$) 3.83 (dd, 1 H, 6-H$_b$, $J_{5,6}$=11.5 Hz, $J_{6Ha-6Hb}$=3.2 Hz) 4.09 (dd, 1 H, J=9.15, 4.4 Hz, 3-H), 4.31-4.39 (m, 1 H, 5-H), 7.2-7.7 (m, 15 H, Ar-H); IR (cm$^{-1}$; Anal. Calcd for C$_{27}$H$_{30}$O$_3$SeSi: C, 63-64; H, 5.93. Found: C, 63.73; H, 5.95.

The β-isomer 3 was obtained in the subsequent fraction in 30.5% yield (0.311 g). H-NMR (CDCl$_3$, 250 MHz) δ 1.04 (s, 9 H, t-Bu); 2.17-2.29 (m, 1 H, 4-H$_a$); 2.58-2.70 (m, i H, 4-H$_b$); 3.65 (m, 2 H, 6-H); 4.03 (t, 1 H, J=9.5 Hz, 3-H); 4.45-4.57 (m, 1 H, 5-H); 7.2-7.5 (m, 9 H, Ar-H); 7.6-7.7 (m, 6 H, Ar-H). IR (cm$_{-1}$): ξ$_{max}$1770. Anal. Calcd for C$_{27}$H$_{30}$O$_3$SeSi: C, 63.64; H, 5.93. Found: C, 63.45; H, 5.96

Isomerization of β-isomer 3 to α-isomer 2

1,8-Diazabicyclo[5.4.0]undec-7-ene (0.167 g, 1.1 mmol) was added to a solution of (S)-5[(t-butyldiphenylsilyloxy)methyl]-3,4-dihydro-3-β-phenylselenenyl-2(5H)-furanone (0.278 g, 0.55 mmol) 3 at 0° C. in THF. The temperature of the solution was allowed to warm slowly to room temperature, and was then stirred at room temperature for 5 h. The reaction was monitored with thin layer chromatography, which indicated that no further isomerization ocurred after 5 hours. The reaction mixture was diluted with ether and then washed with dilute hydrochloric acid and water. The organic layer was dried over anhydrous Na$_2$SO$_4$, and concentrated. The resulting syrup was chromatographed through a column of silica gel (230-400 mesh) using ethyl acetate (0.6%) in hexane as the eluent. Yield of α-isomer: 0.17 g, 61.3%; yield of β-isomer: 0.088 g, 31.6%.

5-O-(t-Butyldiphenylsilyl)-2.3-dideoxy-2-phenylselenenyl-ribose (4)

(S)-5-[(t-Butyldiphenylsilyloxy)methyl]-3,4-dihydro-3-α-phenylselenenyl-2(5H)-furanone 2 (2.2 g, 4.3 mmol) was dissolved in dry toluene (25 mL) and cooled to −78° C. A solution of DIBAL-H in cyclohexane (5 mL, 5 mmol) was added dropwise to the solution under argon over a period of 15 minutes. After the addition was complete, the reaction mixture was stirred at the same temperature for another 15 minutes at which time thin layer chromatography (hexane:ethyl acetate 8.5:1.5) indicated complete disappearance of the starting material. Methanol (3 mL) was added to the reaction mixture and the temperature was allowed to warm slowly to room temperature. Several dropps of a saturated aqueous solution of sodium bicarbonate were then added and the mixture was diluted with ethyl acetate (100 mL). After stirring for another 1.5 hours at room temperature, anhydrous sodium sulphate was added to the mixture, that was then stirred for an additional 4 hours. The mixture was filtered and concentrated under a vacuum to obtain a thick syrup. The syrup was purified by pressing it through a column of silica gel (230-400 mesh) with hexane as the initial eluent, followed by hexane: ethyl acetate (9:1). Yield 2.13 g, 96%. IR (cm$^{-1}$): λ$_{max}$ 3600 (broad, OH); $^1$H NMR (CDCl$_3$, 90 MHz): δ 1.01, 1.06 (s, 9 H, t-Bu); 1.9-2.9 (m, 2 H, 3-H); 3.4-4.2 (m, 3 H, 5-H and 2-H); 5.40 (d, 1-H); 5.50 (t, 1-H); 5.50 (t, 1-H); 7.2-7.8 (m, 15 H, Ar, H). Anal. Calcd for C$_{27}$H$_{32}$O$_3$SeSi: C, 63.39; H, 6.30. Found: C, 63.47; H, 6.32.

1-O-Acetyl-2,3-dideoxy-2-phenylselenenyl-5-O-(t-butyldiphenylsilyl)ribose (5)

Acetic anhydride (1 mL, 9.8 mmol) was added to a solution of 5-O-(t-butyldiphenylsilyl)-2,3-dideoxy-2-phenylselenenylribose 4 (2.13 g, 4.1 mmol) in dry pyridine (15 mL) at 0°-5° C. The reaction mixture was stirred at −78° C. for 8 hours, at which time thin layer chromatography (silica gel: hexane/ethyl acetate) (8.5:1.5) indicated complete disappearance of the lactol 5. Pyridine was removed under reduced pressure and then coevaporated once with toluene. The residue was diluted with ethyl acetate, and then washed successively with dilute sulphuric acid, saturated aqueous sodium bicarbonate and water. The organic layer was dried and the solvent was removed under reduced pressure to get the acetate 5. Yield 2.27 g, 98.7%. $^1$H NMR (CDCl$_3$, 90 MHz): δ 0.97, 1.05 (s, 9 H,t-Bu); 1.85, 2.10 (s, 3 H, —OCOH$_3$); 1.9-2.7 (m, 2 H, 3-H); 3.5-4.0- (m, 3 H, 2-H, 5-H); 4.40 (m, 1 H, 4-H); 6.28 (s, 1-H); 6.46 (d, 1-H); 7.2-7.8 (m, 15 H, AR-H).

5'-O-t-Butyldiphenylsilyl)-3'-deoxy-2'-phenylselenenyl-thymidine (6 and 7)

Method A: Condensation with trimethylsilyl triflate in 1,2-dichloroethane. Thymine (0.454 g, 3.6 mmol) was suspended in hexamethyldisilazane (15 mL) and refluxed with a catalytic quantity of ammonium sulphate. A clear solution was obtained after about 3 hours. Tefluxed was continued for another hour and then the solution was cooled to room temperature. Hexamethyldisilazane was removed under reduced pressure. The residue obtained was coevaporated once with toluene, and then dissolved in dry dichloroethane (8 mL). The silylated thymine solution was mixed with a solution of the acetate 5 (0.99 g, 1.8 mmol) in dichloroethane (8 mL). The mixture was cooled in an ice-water bath and maintained under argon. Trimethylsilyl triflate (0.3 mL; 1.4 mmol) was then added to the mixture dropwise through a syringe with stirring over a period of 20 minutes. The reaction mixture was stirred at 0° C. for 15 minutes and then at room temperature for 15 minutes, at which time the thin layer chromatography (silica: hexane: ethyl acetate 9:1) indicated complete disappearance of the starting material. 5 The reaction was quenched by pouring it into a bilayer of saturated solution of sodium bicarbonate and ethyl acetate with stirring. The two layers were separated and the aqueous layer was extracted once with ethyl acetate. The combined organic layers were washed with a sodium bicarbonate solution, water and then with brine a solution. After drying over anhydrous sodium sulphate, the solvent was removed under reduced pressure. The thick syrup that was obtained was chromatographed through silica gel and hexane, followed by hexane/ethyl acetate (6:1, 4:1) as the eluent. The UV absorbing fractions were pooled and evaporated to get a mixture of B and o anomers, 6 and 7, respectively, as a foamy solid. Yield: 0.86 g; 78%. $^1$H NMR (CDCl$_3$, 90 MHz): δ 1.11 (s, 9 H, t-Bu): 1.45 (s, 3 H, 5-CH$_3$); 1.95–2.70 (m, 2 H, 3'-H); 3.60–4.3 (m, 4 H, 2'-H, 4'-H, 5'-H); 6.16 (d, 1 H, 1'-H, $J_{1,02}$ = 8.1 Hz); 7.15–7.70 (M, 16 H, Ar-H, 6-H); 8.31 (br s, 1-H, -NH, D$_2$O exchangeable). UV (MeOH): $\mu_{max}$ 266.0 nm (ε 4619). Anal. Calcd for C$_{32}$H$_{36}$N$_2$O$_4$SeSi: C, 62.02; H, 5.86; N, 4.52. Found: C, 61.94; H, 5.89; N, 4.49.

Method B: Condensation with anhydrous stannic chloride in acetonitrile. To a solution of the anomeric acetates 5 (3.17 mmol) and 5-methyl-2,4-bis(trimethylsiloxy)-pyrimidine (4.2 g, 15.5 mmol) in dry CH$_3$CN (125 mL) is added Tin (IV) chloride (0.55 mL, 4.7 mmol) under argon. The reaction mixture is stirred at room temperature until the TLC indicates the completion of reaction. The solution is then filtered, and the filtrate is neutralized with a 5% NaHCO$_3$ solution and extracted with ethyl acetate (50 mL×4). The ethyl acetate extract is dried (MgSO$_4$) and concentrated, and the product purified by column chromatography.

Isolation of 7 (R=H) from 6

The β-anomer 6 was isolated by the following procedure. Approximately 70 mg of the mixture of 6 and 7 was dissolved in THF (1 mL) and treated with drops of tetra-butylammonium fluoride until thin layer chromatography (chloroform:methanol 9.5:0.5) indicated the disappearance of the starting material. The solvent was then removed and the crude mixture was separated by preparative thin layer chromatography (3% methanol in chloroform, eluted four times). The minor and the major products were isolated. The minor product 7 showed the following NMR. 1H-NMR (CDCl$_3$, 90 MHz): δ 1.72 (d, 3 H, 5-CH$_3$, J = 1 Hz); 1.8–2.2 (m, 2 H, 3'-H); 3.4–3.8 (m, 2 H, 5'-H); 3.9 (m, 1 H, 2'-H); 4.3–4.6 (m, 1 H, 4'-H); 6.21 (d, 1 H, J=5.5 Hz, 1'-H); 7.27–7.7 (m, 6 H, Ar-H, 6-H).

5'-O-(t-Butyldiphenylsilyl)-3'-deoxy-2',3'-didehydro-thymidine (8)

5'-O-(t-Butyldiphenylsilyl)-3'-deoxy-2'-phenyl-selenenylthymidine 6 (0.496 g, 0.8 mmol) was dissolved in dichloromethane (5 mL) containing a catalytic amount of pyridine (1 drop). The solution was cooled in an ice-water bath. A 30% solution of hydrogen peroxide (0.5 ml, 0.150 g H$_2$O$_2$, 4.4 mmol) was diluted with water (1 mL), and then added dropwise to the solution of 6 over a period of 20 minutes with stirring. The reaction was monitored by thin layer chromatography (CH$_2$Cl$_2$/CH$_3$OH: 9.5/0.5). The temperature of the reaction mixture was allowed to warm slowly to 20° C. and was then stirred at room temperature for one-half hour. The reaction mixture was then diluted with dichloromethane, washed with water, a saturated NaHCO$_3$ solution and with water. After drying over anhydrous Na$_2$SO$_3$, the solvent was removed and the residue was chromatographed through a column of silica gel (230–400 mesh) eluting first with dichloromethane and then with 2–3% dichloromethane to obtain 8 as a thick syrup. Yield 0.283 g, 76%. $^1$H NMR (CDCl$_3$, 90 MHz): δ 1.08 (s, 9 H, C—(CH$_3$)$_3$); 1.49 (d, 3 H, 5-CH$_3$, J = 1.3 Hz); 3.90 (d, 2 H, 5'-H, J=4.2 Hz); 4.92 (m, 1 H, 4'-H); 5.89 (m, 1 H, 2'-H); 6.35 (m, 1 H, 3'-H); 7.00 (M, 1 H, 1'-H); 7.14 d, 1 H, 6-H, J=1.3 Hz); 7.25–7.17 (m, 10 H, Ar-H); 9.00 (br s, 1 H, NH). Anal. Calcd for C$_{26}$H$_{30}$N$_2$O$_4$[0.8 (C$_2$H$_5$)$_2$O]: C, 67.13; H, 7.33; N, 5.36. Found C, 67.03; H, 6.98; N, 5.35.

3'-Deoxy-2',3'-didehydrothymidine (9)

A 1M solution of tetra-butylammonium fluoride in THF (0.4 mL, 0.4 mmol) was added to a solution of 5'-O-(t-butyldiphenylsilyl)-3'-deoxy-2',3'-didehydro-thymidine (0.18 g, 0.39 mmol) in THF. The reaction mixture was stirred at room temperature for 3 hours, after which thin layer chromatography (chloroform/methanol: 9.5/0.5) indicated complete disappearance of the starting material. The reaction mixture was concentrated to dryness and the crude syrup obtained was passed through a vacuum column packed with silica gel. The column was eluted with chloroform (200 mL) followed by 3% methanol in chloroform (200 mL) and finally with 4% methanol in chloroform. Compound 8 was obtained from the final eluent. The product was crystallized from a mixture of ethanol and ether. The first batch of crystals weighed 0.062 grams. The second crop weighed 0.006 g. The total yield was 78%. 1H NMR (DMSO-d$^6$, 90 MHz): δ 1.73 (s, 3 H, 5-CH$_3$): 3.61 (m, 2 H, 5'-H): 4.99 (t, 1 H, 5'-H, 5'-OH, D$_2$O exchangeable); 5.91 (m, 1 H, 2'-H); 6.38 (m, 1 H, 3'-H); 6.82 (m, 1 H, 1'-H); 7.64 (s, 1 H, 6-H); melting point 174° C. UV (H$_2$O): λ$_{max}$ 266.0 nm(ε 10149). [α]$_D$ −39.4 (c=0.701, H$_2$O).

5'-O-(t-Butyldiphenylsilyl)-3'-deoxythymidine (10)

Tri-butyltin hydride (0.18 mL, 0.67 mmol), followed by a 1M solution of triethyl borane in hexanes (0.5 mL, 0.5 mmol) were added under argon to a suspension of 5'-O-(t-butyldiphenylsilyl)-3'-deoxy-2'-phenyl-selenenylthymidine 6 (0.282 g, 0.45 mmol) in anhydrous benzene. The reaction mixture slowly became clear.

After 4 hours of stirring, thin layer chromatography (CH$_2$Cl$_2$/MeOH: 9.5/0.5) indicated complete disappearance of the starting material. The reaction mixture was diluted with acetonitrile then was concentrated to a thick syrup. The syrup was chromatographed through a column of silica gel (230-400 mesh), eluting first with dichloromethane, followed by 3% methanol in dichloromethane. Compound 10 was isolated as a foamy solid. Yield 0.186 g, 89%. $^1$H NMR (CDCl$_3$, 90 MHz): δ 1.10 (s, 9 H, t-Bu); 1.65 (d, 3 H, 5-CH$_3$, J=1.1 Hz); 1.9-2.4 (m, 4 H, 2' and 3'-H); 3.7-4.3 (m, 3 H, 4' and 5'-H); 6.11 (pseudo t, 1 H, 1'-H, J=4 Hz); 7.26 (s, 1 H, 6-H); 7.4-7.9 (m, 10 H, Ar-H); 8.32 (br s, 1 H, NH). Anal. Calcd for C$_{26}$H$_{32}$N$_2$O$_4$: C, 67.21; H, 6.94; N, 6.03. Found: C, 67.09; H, 6.96; N, 6.01.

3'-Deoxythymidine (11)

A 1M solution of tetra-butylammonium fluoride in THF (0.35 mL, 0.35 mmol), was added to a solution of 5'-O-(t-butyldiphenylsilyl)-3'-deoxythymidine (0.162 g, 0.35 mmol) in THF (3 mL). The reaction mixture was stirred at room temperature for 3 hours, at which time thin layer chromatography indicated complete disappearance of the starting material. The solvent was removed under reduced pressure. The residue was dissolved in a minimum volume of chloroform and then purified by passing it through a vacuum column packed with silica gel. The column was eluted with methanol, followed by 6% methanol in chloroform. Compound 11 was obtained from the final eluent as a white crystalline solid. The product obtained was twice crystallized from ethyl acetate. Yield 0.063 g, 80%. $^1$H NMR (DMSO-d6, 90 MHz): δ 1.77 (s, 3 H, 5-CH$_3$); 1.7-2.3 (m, 4 H, 2' and 3' H); 3.60 (m, 2 H, 5'-H); 4.00 (m, 1 H, 4'-H); 5.01 (t, 1 H, 5'-OH, J=5.4 Hz, D$_2$O exchangeable); 5.95 (dd, 1 H, 1'-H, J=5.5 and 6.5 Hz); 7.79 (s, 1 H, 6-H); 11.20 (br s, 1 H, NH, D$_2$O exchangeable); mp 151°-152° C.; [α]$_D$+18.3(c=0.999, MeOH).

EXAMPLE 2

Preparation of 2',3'-Dideoxy-2',3'-Didehydrothymidine

The method of Example 1 is followed with the exception that phenyl disulfide is substituted for phenylselenium bromide.

EXAMPLE 3

Preparation of 2',3'-Dideoxy-2',3'-Didehydrothymidine

The method of Example 1 is followed with the exception that t-butyl disulfide is substituted for phenylselenium bromide.

EXAMPLE 4

Preparation of 2',3'-Dideoxyuridine

Compound 5 is prepared as described above.

Method A: Condensation of compound 5 with the base using anhydrous stannic chloride in acetonitrile. To a stirred solution of the anomeric acetates 5 (3.17 mmol) and 2,4-bistrimethylsilyluracil (1.6 g, 6 mmol) in acetonitrile (50 mL, dried over 4A molecular sieves) is added anhydrous stannic chloride (1.65 g, 6.34 mmol). The reaction mixture is allowed to stir at room temperature with protection from moisture until TLC indicates the completion of reaction. When the reaction is complete, the reaction mixture is diluted with a saturated sodium bicarbonate solution (25 mL) and then extracted with ethyl acetate. The solvent layer is dried (MgSO$_4$), filtered and concentrated. The residue is purified by chromatography. The resulting 5'-O-(t-butyldiphenylsilyl)-3'-deoxy-2'-phenylselenenylthymidine is then treated as described in Example 1 to produce D2U or D4U.

Method B: Condensation of compound 5 with the base using trimethylsilyl triflate in acetonitrile. A mixture of anomeric acetates 5 (0.4 mmol) and 2,4-bis-trimethylsilyloxy pyrimidine (0.35 g, 1.37 mmol) in dry acetonitrile (15 mL) is treated with trimethylsilyl triflate (0.149 g, 0.67 mmol) at room temperature under argon until TLC indicates that the reaction is completed. Treatment of the reaction mixture as described under method A followed by chromatographic purification provides 5'-O-(t-butyldiphenylsilyl)-3'-deoxy-2'-phenylselenenylthymidine is then treated as described in Example 1 to produce D2U or D4U.

Method C: Condensation of compound 5 with the base using trimethylsilyl triflate in ClCH$_2$CH$_2$Cl. Compound 5 (3 mmol) is reacted with 2,4-bistrimethylsilyloxy pyrimidine (2.0 g, 7.8 mmol) in the presence of trimethylsilyl triflate (1.15 g, 5.2 mmol) in dry ClCH$_2$CH$_2$Cl (20 mL) according to the procedure described in Method B.

EXAMPLE 5

Preparation of 2',3'-Dideoxyinosine and 2',3'-Dideoxy-2',3'-Didehydroinosine

2',3'-Dideoxyinosine and 2',3'-dideoxy-2',3'-didehydroinosine are prepared as described in Example 1 with the substitution of silylated hypoxanthine for silylated thymine.

EXAMPLE 6

Preparation of 2',3'-Dideoxyadenosine and 2',3'-Dideoxy-2', 3'-didehydroadenosine 2',3'-Dideoxyadenosine and 2',3'-dideoxy-2',3'-didehydroadenosine are prepared as described above for synthesis of D2T and D4T with the substitution of silylated adenosine for silylated thymine.

This invention has been described with reference to its preferred embodiments. Variations and modifications of the method of stereoselective glycosylation of heterocyclic bases will be obvious to those skilled in the art from the foregoing detailed description of the invention. It is intended that all of these variations and modifications be included within the scope of the appended claims.

I claim:
1. A method for the stereoselective glycosylation of heterocyclic bases, comprising the steps of:
   i) providing 5-O-protected-3,4-dihydro-2(5H)-furanone;
   ii) reacting 5-O-protected-3,4-dihydro-2-(5H)-furanone with a strong base and silyl halide to produce the corresponding 1-silyl enol ether;
   iii) reacting the 1-silyl enol ether with a compound selected from the group consisting of an aromatic selenenyl halide and a C$_1$ to C$_{25}$ aliphatic selenenyl halide to produce a 5-O-protected-3,4-dihydro-3-α-(aromatic or aliphatic)-selenenyl-2(H)-furanone;
   iv) reducing the furanone to a furanose;
   v) activating the 1 position of the furanose by replacing the 1-OH group with a moiety selected from the group consisting of halide, O-acyl, and O-alkyl; and
   vi) condensing the activated furanose with a protected heterocyclic base.

2. The method of claim 1, wherein the aromatic selenenyl halide is phenyl selenenyl halide.

3. The method of claim 1, wherein the heterocyclic base is selected from the group consisting of purines and pyrimidines.

4. The method of claim 3, wherein the heterocyclic base is selected from the group consisting of adenosine, hypoxanthine, $N^6$-alkyl prine, $N^6$-halopurine, guanine, thymine, cytosine, 6-azapyrimidine, 2-mercaptopyrimidine, and uracil.

5. The method of claim 1 wherein the heterocyclic base is protected with a moiety selected from the group consisting of trimethylsilyl, dimethylhexylsilyl, t-butyldimethylsilyl, t-butyldiphenylsilyl, alkyl groups, acyl groups, methyl sulfonyl, and p-toluylsulfonyl.

6. The method of claim 1 wherein the 5-O-position is protected with a moiety selected from the group consisting of trimethylsilyl, dimethylhexylsilyl, t-butyldimethylsilyl, t-butyldiphenylsilyl, tritylmethyl, alkyl groups, acyl groups, methyl sulfonyl, and p-toluylsulfonyl.

7. The method of claim 1, wherein the silyl enol ether is prepared by reacting the furanone with lithium bis(trimethylsilyl)amide and a silyl halide.

8. The method of claim 1, wherein the selenenyl group is removed oxidatively to produce a 2',3'-dideoxy-2',3'-didehydronucleoside.

9. The method of claim 1, wherein the selenenyl group is removed reductively to produce a 2',3'-dideoxynucleoside.

10. The method of claim 1, wherein the condensation reaction is carried out in the presence of a compound selected from the group consisting of trimethylsilyl triflate, $SnCl_4$, $ZnCl_4$, $TiCl_4$ $AlCl_3$, $FeCl_3$, $BF_3$-diethyl ether, and $BCl_3$.

* * * * *